United States Patent [19]

Steffens

[11] 4,144,623
[45] Mar. 20, 1979

[54] PROCESS FOR THE PRODUCTION OF TAMPON BLANKS

[76] Inventor: Bert Steffens, Jaugel 5, D-5470 Andernach 13, Fed. Rep. of Germany

[21] Appl. No.: 810,569

[22] Filed: Jun. 27, 1977

[30] Foreign Application Priority Data

Jun. 30, 1976 [DE] Fed. Rep. of Germany ....... 2629381

[51] Int. Cl.² .............................................. A61F 13/20
[52] U.S. Cl. ....................................................... 28/118
[58] Field of Search ......................... 28/118, 119, 120; 128/270, 285

[56] References Cited

U.S. PATENT DOCUMENTS

| | | | |
|---|---|---|---|
| 1,731,665 | 10/1929 | Heubsch | 28/120 |
| 2,328,795 | 9/1943 | Finks | 128/285 X |
| 3,011,495 | 12/1961 | Brecht | 28/118 X |
| 3,874,031 | 4/1975 | Simon | 28/119 |

Primary Examiner—Dorsey Newton
Attorney, Agent, or Firm—Cushman, Darby & Cushman

[57] ABSTRACT

There is set forth a process for the production of a tampon, particularly for menstrual hygiene in which a fleece of absorbent cotton or similar material is wound up together with a retrieving string arranged on it. A fleece track is carried along approximately horizontally by a conveying device, a string coming from a supply roll is placed on the fleece track to be carried along in the direction of conveyance and subsequently cut off on the fleece track into a retrieving string, whereupon one part of the retrieving string is pressed onto the fleece track and the other part of the retrieving string is turned and whereupon the fleece is torn off the fleece track and wound up on a winding pin together with its retrieving string. There is also described an apparatus for carrying out the process.

11 Claims, 7 Drawing Figures

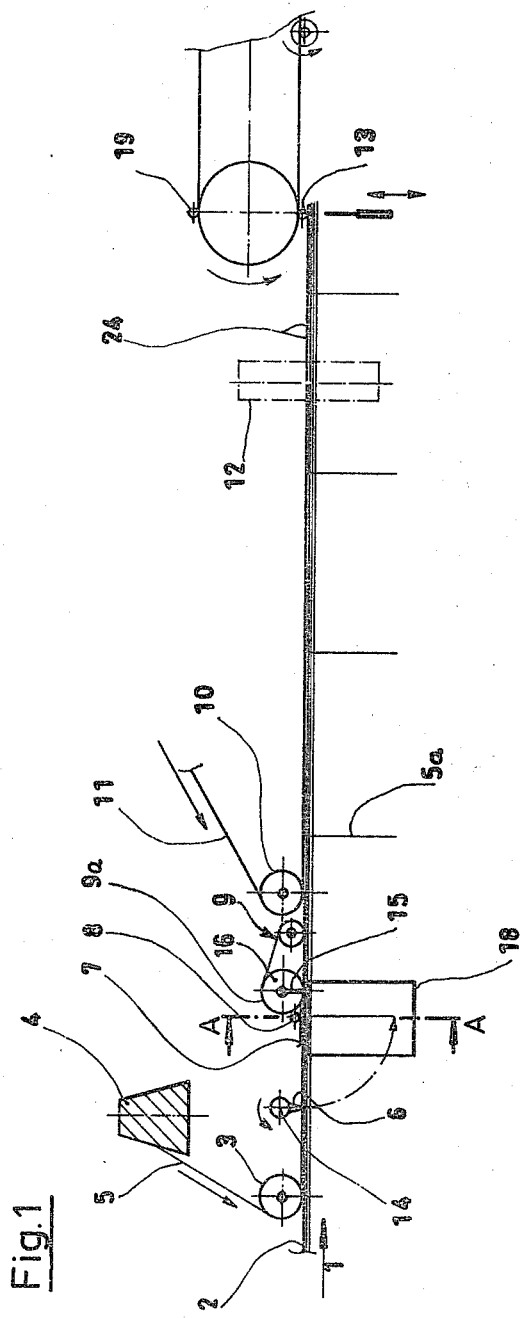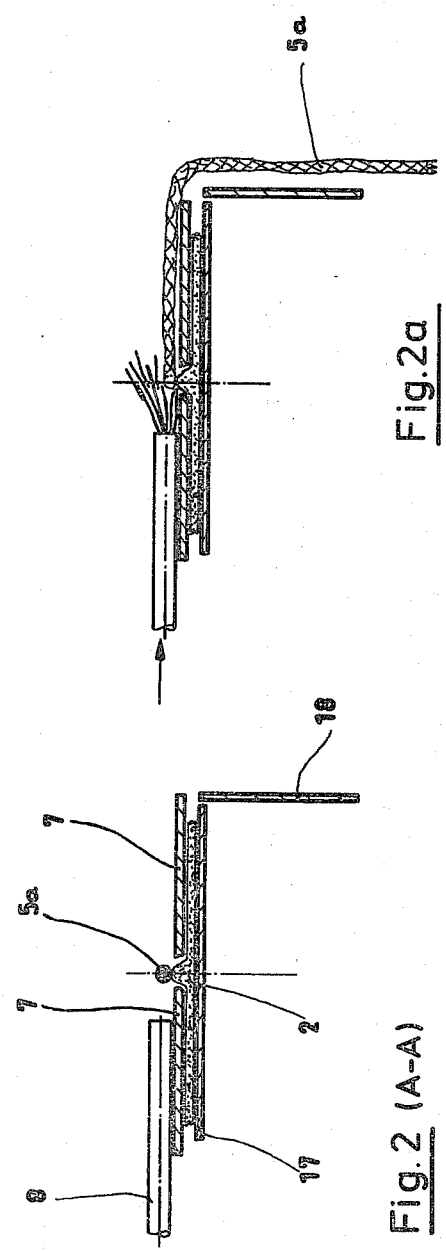

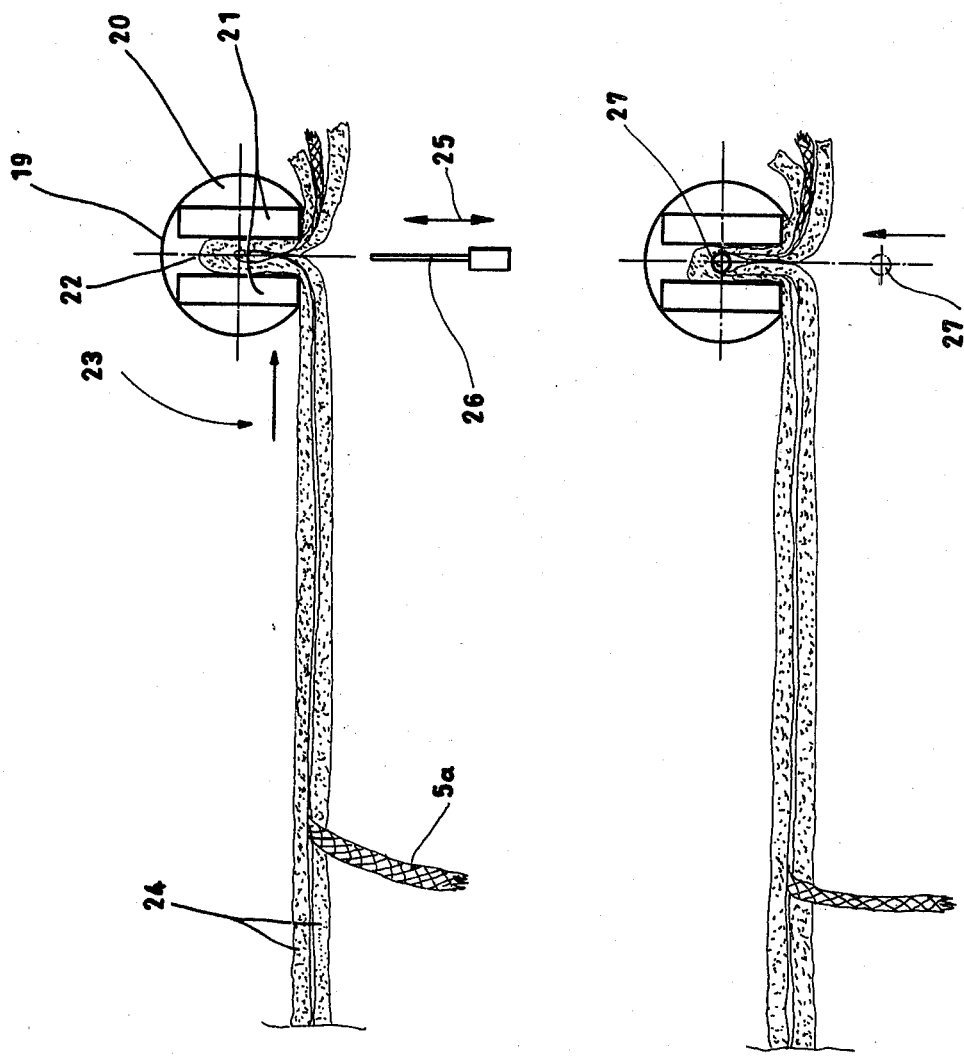

PROCESS FOR THE PRODUCTION OF TAMPON BLANKS

BACKGROUND OF THE INVENTION

The invention is directed first to a method for the production of a tampon, particularly for menstrual hygiene, in which a fleece made from absorbent cotton or similar material is wound up with an attached retrieving string.

Insofar as methods of this type have become known, it is found that the joining of the fleece and the retrieving string before they are wound up is always a more or less complicated process which in any case does not in the final analysis permit continuous production. The problem is rooted in the fact that the retrieving string must survive further processing together with the fleece such as winding, compressing, etc., undamaged and have a secure anchorage in the finished tampon for later handling.

There are also, however, proposals for the improvement of this process, one of which is of the applicant himself (cf. DT-OS No. 2 409 218) and is characterized by a simplified arrangement for the retrieving string with simultaneous secure fastening by means of a constricting effect. But even this proposal still does not permit a continuous procedure. It provides that the retrieving string be set into the fleece by means of a hollow needle and held in place by it. But this joining can only be effected in cycles.

The task of the invention is to propose a method of the type mentioned at the outset, which permits continuous production with undiminished fastening of the retrieving string in the finished tampon. A further task is to specify a device for carrying out the invented method.

SUMMARY OF THE INVENTION

The task is accomplished by having a fleece track carried along approximately horizontally by a conveying device, a string coming from a supply roll being placed on the fleece track to be taken along in the direction of conveying and being subsequently cut off into lengths on the fleece track to form the retrieving string. One part of the retrieving string is thereupon pressed on to the fleece track and the other part of the retrieving string is turned around, and a piece of fleece is thereupon torn off from the fleece track and wound up on a winding pin together with its retrieving string.

It is advantageous to place the string approximately in the middle of the fleece track. In a further form of the idea of the invention, the fleece track is pressed down to both sides of the part of the retrieving string to be turned around. It is more practical for the part of the retrieving string to be turned around to be turned pneumatically. In another proposal the part to be turned around of the retrieving string is turned around mechanically.

In a further development of the idea of the invention, the fleece is torn off from the fleece track at the cutoff point for the retrieving string. It is advantageous for the string to be cut into lengths on the fleece track and the fleece track partially cut through simultaneously.

In another proposal, the fleece together with its retrieving string is combed into the winding pin by means of a stick or choke, the stick or choke being designed to remain in the finished tampon.

After a part of the retrieving string is turned around, it is advantageous to place a second fleece track on the one already present to form a two-layered fleece track and tear a two-layered fleece off from this.

The apparatus according to the invention is characterized by the arrangement over a horizontal conveyor for the transport of a fleece track, viewed in the direction of the conveying, of a device for placing string coming from a supply roll, a cutting device for cutting the string carried along with the fleece track into lengths for a retrieving string, a device for turning around one part of the retrieving string, a device for holding the other part of the retrieving string, a tearing device and a winding device.

Suitably, the device for placing the string is a roll running synchronized with the fleece track. In another proposal, the cutting device is a rotating knife whose axis of rotation is perpendicular to the direction of the conveyance.

It is advantageous for the device for turning to be a smooth-stream nozzle arranged transverse to the direction of conveyance.

In a further development of the idea of the invention, pressing plates for the fleece track are arranged in the area of the turning device at both sides of the retrieving string.

It is advantageous for the holding device to be a pair of driven conveyor drums. It is especially advantageous if the first conveyor drum has a deflecting plate for the part of the retrieving string which is turned around.

The advantages of the invention include, among other things, the fact that the process of joining the retrieving string and the fleece was substantially simplified and the possibility created of continuous production.

BRIEF DESCRIPTION OF THE DRAWINGS

Further advantages and details are described by means of the drawings for a preferred form of a device according to the invention. In the drawings:

FIG. 1 is a schematic side view of the device;

FIG. 2 is a section along the line A—A of FIG. 1;

FIG. 2a is the same as FIG. 2 except that it is at the moment when the retrieving string is turned around;

FIG. 3 is a side view of a two-layered fleece after being combed into a winding pin by means of a slide;

FIG. 4 is the side view of a two-layered fleece in the same state as the subject of FIG. 3 but with the difference that it is combed in by means of a stick.

Figure 2B:
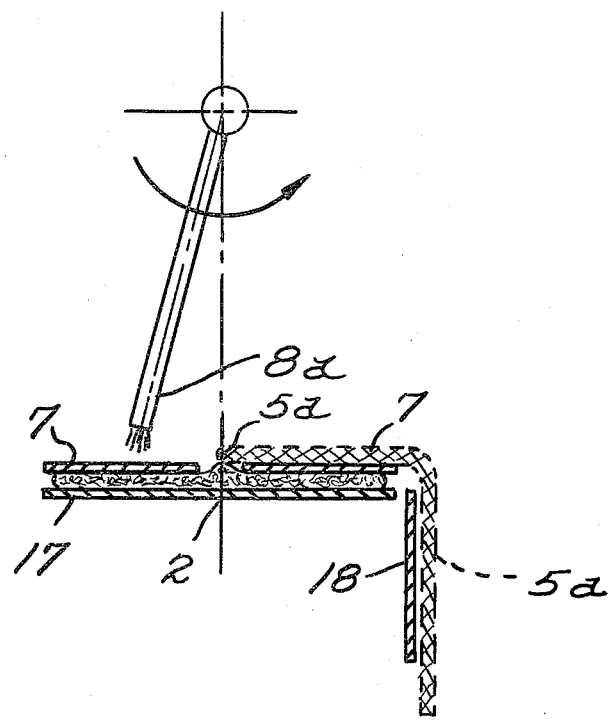
FIG. 2b is a schematic side view of mechanical apparatus for turning the retrieving string.

Referring more specifically to the drawings, the device in FIG. 1 consists in the first instance of a horizontal conveyor generally indicated as 1. An arrow represents the direction of conveyance. The horizontal conveyor can be a belt conveyor, a roller conveyor or something similar. It conducts a fleece track 2, which comes from a card (not shown) to the further processing stations. These are arranged over the horizontal conveyor. In detail, there is a roll 3 for placing a string 5 coming from a supply roll 4; a rotating knife 6 for cutting into lengths the string 5, which is carried along by the fleece track 2, to form a retrieving string 5a; pressing plates 7; a smooth-stream nozzle 8 for pneumatically reorienting a portion of string 5a relative the direction of conveyance; a pair of conveyor drums 9; a device 10 for mounting a second fleece track 11; a tearing device 12 and a winding device 13.

The roll 3 is driven so as to permit it to run synchronized with the fleece track 2. The rotating knife 6 has an axis of rotation 14 which is perpendicular to the direction of conveyance of the fleece track 2.

The pair of conveyor drums 9 is also driven so as to permit synchronized running with the fleece track 2. Looking in the direction of conveyance, the first conveyor drum 9a has a deflecting plate 15 (i.e., stop plate) which operates on the part of the retrieving string 5a which is turned around (reoriented by nozzle 8. The deflecting plate 15 should deflect the part of the retrieving string 5a which is turned around if it is ever turned too much, i.e., more than at right angles to the direction of conveyance. For this purpose, the deflecting plate is placed approximately perpendicularly on the face 16 of the first conveyor drum, extending in a radial direction to the periphery. The circumference of the first conveyor drum is several times the length of the retrieving string 5a such that the deflecting plate 15 always comes into a vertical position when the retrieving string 5a is supposed to be turned around. Thus, where the reoriented portion of string 5a is turned back more than 90° (the angle between plate 15 and the direction of conveyance) the reoriented portion of string comes into contact with plate 15 and is deflected into the desired 90° orientation.

The tearing device 12 is only schematically represented because various conventional embodiments can be used here. The winding device 13 is also only indicated as regards its arrangement. Further details proceed from the following description of the figures.

In FIG. 2, the fleece track 2 is pressed down on the horizontal conveyor 1, which is here represented with a supporting surface 17 and a side shielding 18, by means of the pressing plates 7 to both sides of the retrieving string 5a. The consequence of this is that the retrieving string 5a lies raised in the area of the pressing plates 7 on the part of the fleece track 2 which is not pressed down. Over one of the pressing plates 7 is arranged the smooth-stream nozzle 8, which reaches close to the retrieving string 5a. With its aid a part of the retrieving string 5a can be safely turned as represented in FIG. 2a.

FIG. 3 shows an essential component of the winding device 13, namely, a known winding pin 19. The winding pin 19 consists of a front plate 20 to which two parallel flat bars 21 of iron are attached which form a slit 22. The winding pin 19 is driven and is on the one hand rotated in the direction of the arrow 23 and on the other carried along in the direction of conveyance.

Figure 3A:
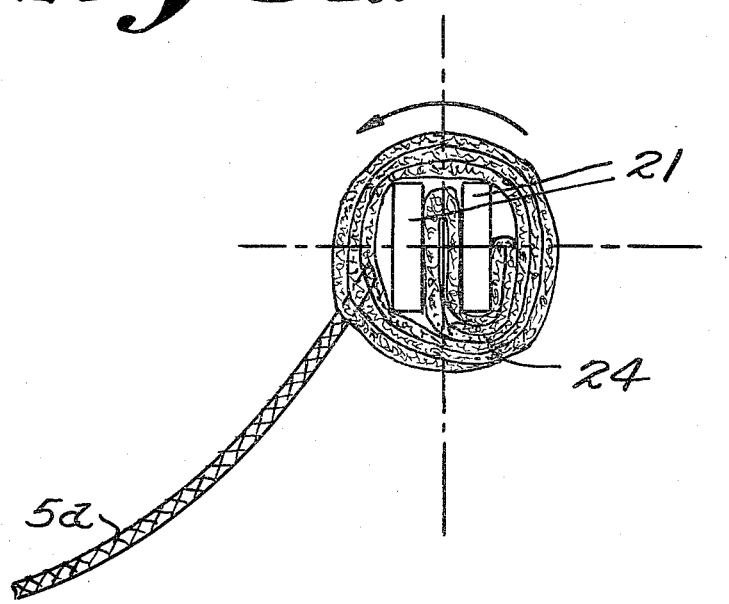
FIG. 3a depicts the fleece track wound on the winding pin.

FIG. 3 represents the moment in which the actual winding process beings. For this purpose, a fleece 24, which has been torn off from the two-layered fleece track 2/11 or is yet to be torn off, has been partially combed into the slit 22 of the winding pin 19 by means of pusher 26 going up and down in the direction of the double arrow 25. The winding process is further illustrated in FIG. 3a, showing fleece track 24 wound about winding pin 19 to form a tampon blank.

FIG. 4 shows another proposal of the invention in which the combing is done by a stick or choke 27, the stick or choke 27 being designed to remain in the finished tampon.

The operation of the apparatus depicted in FIGS. 1-4 is as follows.

First, a fleece track 2 is placed on the conveying device 1 and carried along by it approximately horizontally. Then a string 5 is placed on the fleece track 2 from above, preferably in the middle of the fleece track. The string 5 is cut on the fleece track 2 into a retrieving string 5a. Then one part of the retrieving string 5a is pressed on to the fleece track 2, and the fleece track 2 is simultaneously pressed down to both side of the other part of the string and the part of the retrieving string 5a lying raised on the part of the fleece track 2 which is not pressed down, is pneumatically turned, e.g., by blowing air through nozzle 8. In another form of the invention the turning is done mechanically. A suitable mechanical string turning appratus will be described in conjunction with FIG. 2b. Further on, the turning point with its adjoining areas also comes into the zone in which one part of the retrieving string 5a was previously pressed on to the fleece track 2 and is pressed flat leg conveyor drums 9.

Not essential to the invention but still advantageous is the next stop in which a second fleece track 11 is mounted on the already present fleece track 2 from above. The second fleece track 11 preferably has the same width as the first fleece track 2. The retrieving string or string 5a are largely covered by the second fleece track 11 and remain still visible only insofar as they extend beyond a longitudinal edge of the tow-layered fleece track 2/11 with a free end. With its forward end the two-layered — in other cases one-layered — fleece track 2/11 is combed into the slit 22 of a winding pin 19 together with the retrieving string 5a and held there.

Then, in other cases even beforehand, a fleece 24 is torn off the two-layered fleece track 2/11 and subsequently wound. The tearing off is preferably done at the earlier cutoff point for the retrieving string 5a. To facilitate the tearing off, the fleece track 2 in another proposal is already partially cut through simultaneously with the cutting of the string 5. In order to give the retrieving string 5a a secure fastening in the finished tampon, the latter, as is already known, must receive the possibility for an adequate constriction of the tampon. An interrelation between the turning and winding of the retrieving string 5a exists insofar as that, for example, with a long unturned part of the retrieving string 5a combing and winding do not necessarily have to take place at the beginning of the retrieving string 5a.

As noted above, retrieving string 5a can be reoriented with respect to the direction of conveyance by mechanical apparatus rather than pneumatic nozzle 8. Such mechanical apparatus are well known in the art and suitable apparatus is illustrated in FIG. 2b. More specifically, reorientation of string 5a is effected through a driving rod 8a, rotating at a predetermined rate through a plane transverse to the direction of conveyance. Rod 8a suitably rotates in synchronism with movement of the conveyor. As driving rod 8a rotates across the center of the fleece track, string 5a is brushed by the rod, causing it to reorient relative the direction of conveyance.

What is claimed is:

1. A method for the production of a tampon blank particularly adapted for menstral hygiene wherein a fleece made from absorbent cotton or the like is wound up together with a retrieving string arranged on said fleece, said method comprising carrying along a fleece track approximately horizontally by conveying means, supplying a string from a supply roll, placing said supplied string on the fleece track and carrying the string together with the fleece track along in the direction of conveyance, subsequently cutting off the string on the fleece track to form a retrieving string, thereupon pressing one part of the retrieving string onto the fleece track and turning the other part of the retriveing string to a direction transverse to said one part, thereupon tearing off a portion of the fleece track and winding up said torn off fleece track portion together with its retrieving string on a winding pin to form said blank.

2. The method of claim 1 comprising placing said supplied string in the middle of the fleece track.

3. The method of claim 1 comprising pressing the fleece track down to both sides of the part of the retrieving string which is to be turned.

4. The method of claim 3 comprising pneumatically turning the part of the retrieving string to be turned.

5. The method of claim 1 comprising pneumatically turning the part of the retrieving string to be turned.

6. The method of claim 1 comprising mechanically turning the part of the retrieving string to be turned.

7. The method of claim 1 wherein the fleece is torn off the fleece track at the cutoff point for the retrieving string.

8. The method of claim 7 comprising simultaneously cutting off the string on the fleece track and partially cutting through the fleece track.

9. The method of claim 1 comprising partially combing the torn off fleece into the winding pin together with its retrieving string by means of stick means, said stick means being adapted to remain in said tampon blank.

10. The method of claim 3 comprising placing a second fleece track on the already present fleece track after the turning of one part of the retrieving string to form a two-layered fleece track and subsequently tearing off a two-layered fleece from the two-layered fleece track.

11. The method of claim 1 comprising placing a second fleece track on the already present fleece track after the turning of one part of the retrieving string to form a two-layered fleece track and subsequently tearing off a two-layered fleece from the two-layered fleece track.

* * * * *